United States Patent [19]

Emmrich et al.

[11] Patent Number: 4,776,927
[45] Date of Patent: Oct. 11, 1988

[54] PROCESS FOR THE SEPARATION OF AROMATIC HYDROCARBONS FROM A HYDROCARBON MIXTURE

[75] Inventors: Gerd Emmrich; Gerhard Preusser, both of Essen, Fed. Rep. of Germany

[73] Assignee: Krupp=Koppers GmbH, Essen, Fed. Rep. of Germany

[21] Appl. No.: 7,359

[22] Filed: Jan. 27, 1987

[30] Foreign Application Priority Data

Jan. 25, 1986 [DE] Fed. Rep. of Germany ....... 3602240

[51] Int. Cl.$^4$ .......................... B01D 3/40; C07C 7/08; C10G 7/08
[52] U.S. Cl. ........................................ 203/58; 203/84; 203/DIG. 9; 208/313; 208/326; 585/808; 585/860; 585/865
[58] Field of Search ............................. 203/58, 50–57, 203/59–70, DIG. 9, 84; 585/808, 860, 865; 208/313, 326

[56] References Cited

U.S. PATENT DOCUMENTS 2,069,329 2/1937 Roelfsema ............................. 203/58
2,376,870 5/1945 Engel ..................................... 203/58
3,259,555 7/1966 Lankton et al. ....................... 203/60
3,679,579 7/1972 Preusser et al. ...................... 585/808

FOREIGN PATENT DOCUMENTS 1468315 3/1970 Fed. Rep. of Germany ...... 585/808
1291029 9/1972 United Kingdom .

Primary Examiner—Wilbur Bascomb
Attorney, Agent, or Firm—Michael J. Striker

[57] ABSTRACT

A process is disclosed for the separation of aromates from hydrocarbon mixtures of optional aromate content through extractive distillation using N-substituted morpholine displaying substituents having no more than 7 C-atoms as selective solvent. Part of the solvent is delivered to the uppermost plate of the extractive distillation column and the remainder of the solvent, preferably amounting to between 10 and 40% by weight, is introduced into the extractive distillation column in at least two partial streams onto plates above the inlet for the hydrocarbon mixture. The temperature of the respective solvent partial streams is adjusted to neither exceed the temperature of the corresponding delivery plates nor fall below this temperature by more than 10° C.

5 Claims, 2 Drawing Sheets

//PROCESS FOR THE SEPARATION OF AROMATIC HYDROCARBONS FROM A HYDROCARBON MIXTURE

BACKGROUND OF THE INVENTION

The invention concerns a process for the separation of aromates from hydrocarbon mixtures of optional aromate i.e. aromatic hydrocarbons content, employing N-substituted morpholine, the substitutions of which display no more than seven carbon atoms, as selective solvent, by delivering only a part of the required total amount of solvent to the uppermost plate of the extractive distillation column.

The above-described general technique for the recovery of aromates has already been known for many years, and has been well authenticated in the meantime in practice at various large-scale technical plants, particularly using N-formylmorpholine as selective solvent. As indicated from German Patent DE-PS No. 15 68 940, the sump product discharged from the extractive distillation column is normally introduced to a subsequently disposed distilling column, in which the aromates contained therein as extract are distillatively separated from the solvent. The solvent is then discharged from the sump of the distilling column and led back into the extractive distillation column for re-employment. Herewith, the introduction or re-introduction of the solvent follows as a rule at the uppermost plate(s) of the extractive distillation column. The non-aromatic hydrocarbons are, on the other hand, discharged from the top of the extractive distillation column, and can be condensed partially or completely in subsequently disposed condensation arrangements. A variation of this manner of operation is known, moreover, from German Patent DE-PS No. 20 35 771, in which only a part of the selective solvent is delivered to the uppermost plate of the extractive distillation column, while the rest of the solvent, together with the entry product, is introduced into the extractive distillation column by means of the conduit provided for the introduction of entry product.

Whether or not the above-described techniques, as already stated, have been well authenticated in practice, it has remained desirable to optimize further this manner of operation and, indeed, particularly with regard to an increase in the throughput capacity and a more silent operation of the extractive distillation column, as well as an improvement in the results.

In pursuance of this object, it has now surprisingly been discovered that with a technique of the above-described type, such an optimization can be obtained when according to the present invention the part of the total amount of the solvent which is not delivered to the uppermost plate of the extractive distillation column, amounting to between about 10 and 40 percent by weight, distributed into at least two partial streams, is introduced into the extractive distillation column onto plate above the inlet for the hydrocarbon mixtures, and further so adjusting the delivery temperature of the respective partial streams of solvent that they do not exceed the temperature of the corresponding feed plates and also fall no more than 10° C. below said temperature.

SUMMARY OF THE INVENTION

The invention is therefore based upon the knowledge that this optimization is all the more effective indeed the more the delivery of solvent is adapted to the concentrationdependent temperature behavior in the extractive distillation column.

The novel features which are considered characteristic for the invention are set forth in particular in the appended Claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
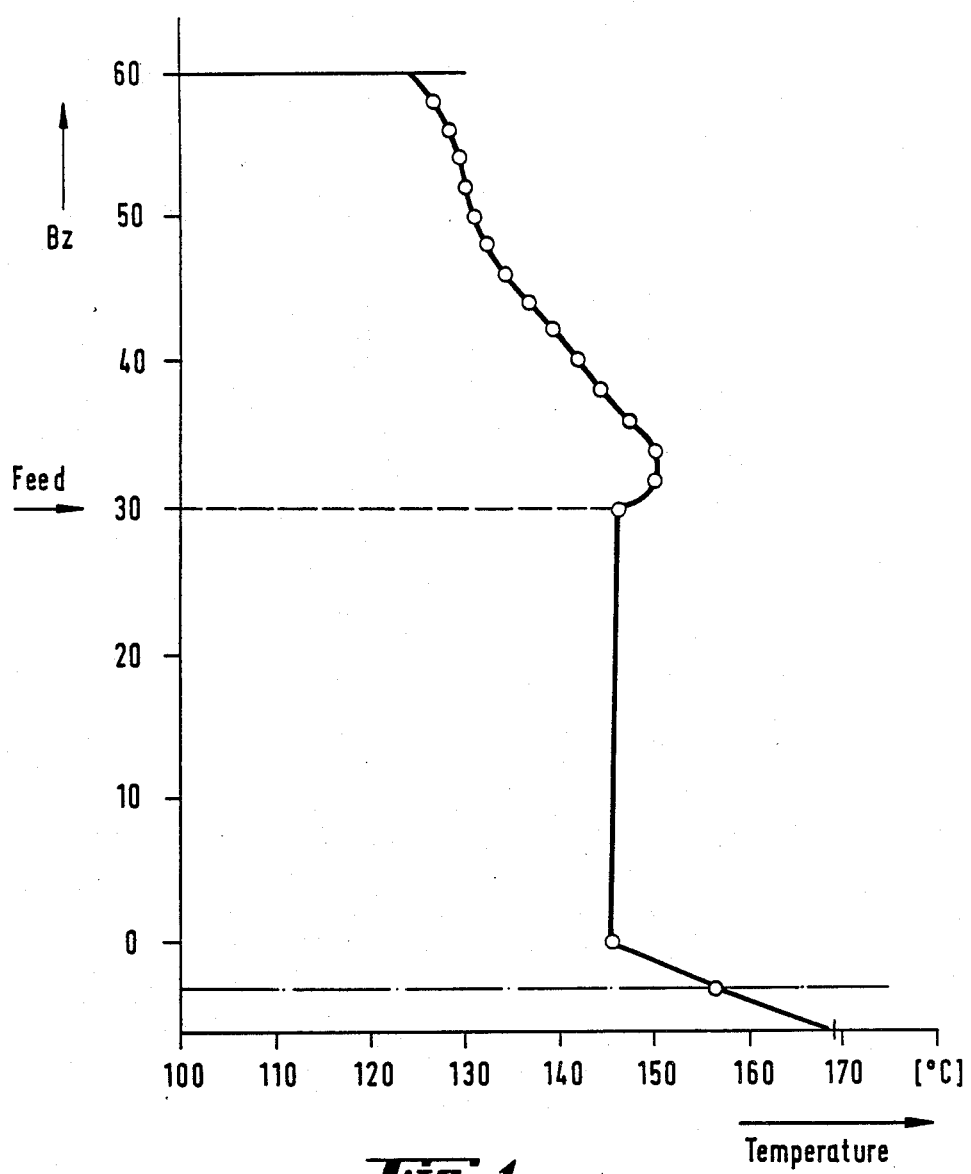
FIG. 1 shows a graphically-represented temperature scheme for an extractive distillation column having 60 plates, in accordance with the present invention.

In FIG. 1 is represented, graphically, as an example, the temperature-behavior for an extractive distillation column provided with 60 plates. Serving as entry product therewith is the benzene fraction of a pyrolysis benzene and, as solvent, N-formylmorpholine. The temperature is set forth at the abscissa and the plate number is indicated along the ordinate. The benzene fraction is introduced in this case at the 30th plate. The shape of the curve proves that in the range of benzene introduction up to the sump of the column, the concentrating of the aromates in the extract becomes hardly noticeable in a temperature elevation, whether or not the highest molar ratio of solvent to entry hydrocarbons is necessary there, since the vapor pressure of the non-aromates there, in contrast to the aromates, must lie as far as possible apart, in order to drive out even the smallest amount of non-aromates from the solution. It is first in both evaporation stages directly across the sump of the extractive distillation column that the temperature increases suddenly in two stages. Above the benzene introduction, the behavior of the temperature curve shows a clear jump. This can be explained in that here, initially, very many aromate vapors go into solution and their condensation heat passes into the solvent. It is first thereafter that the amount of aromate vapor going into solution steadily decreases from plat to plate, and the temperature behavior up to the uppermost plate of the extractive distillation column displays a tendency to drop.

The process according to the present invention utilizes this temperature behavior in the extractive distillation column, in which a delivery of the solvent partial streams which are not supposed to be brought into the uppermost plate of the extractive distillation column is provided in at least two partial streams at plates above the entry product delivery. Herewith it is of decisive importance that the delivery temperature of the solvent always be oriented to the temperature behavior in the column. That is, this temperature cannot exceed the temperature of the corresponding delivery plates, since otherwise, aromates already dissolved in the solvent are again expelled. In all cases, it is permissible for the delivery temperature of the solvent to fall slightly below the temperature at the delivery plates, i.e., about no more than 10° C.

The process according to the present invention utilizes this temperature behavior in the extractive distillation column in that a delivery of the partial stream of solvent which is not introduced to the uppermost plate of the extractive distillation column is provided in at least two partial streams onto plates above the entry product delivery. In connection herewith it is of great significance that the delivery temperature of the solvent always be oriented to the temperature behavior of the column. That is, this temperature cannot exceed the temperature of the corresponding delivery plates, since otherwise aromates already dissolved in the solvent are expelled again therefrom. In all case it is permissible for the delivery temperature of the solvent to fall slightly below the temperature of the delivery plates, i.e., approximately no more than 10° C.

The determination of the delivery points for the individual partial streams of solvent which are supposed to be introduced between the inlet for the hydrocarbon mixture and the uppermost plates of the extractive distillation column is likewise gauged to the temperature behavior of this column. The delivery of the individual partial streams should follow namely, in particular, in the range in which the temperature behavior above the inlet for the hydrocarbon mixture displays the clear jump. In practice, this naturally depends upon the construction and the concrete operational conditions of the particular extractive distillation column. As a rule, however, one can proceed with a presumption that the delivery of the particular partial streams should preferably be effected in the range between the third and tenth plates above the inlet for the hydrocarbon mixture.

As evident from the temperature behavior represented by FIG. 1, the content of aromates from the hydrocarbon inlet plates up to the top of the extractive distillation column continually decreases. This signifies, however, that in order to dissolve the respective residual amounts of aromate an always smaller amount of solvent is necessary. Since the ideal distribution of the amount of solvent in the range between the entry product delivery and the uppermost plates of the extractive distillation column is supposed to be oriented to this behavior, the extent of optimization of the extractive distillation is all the greater indeed, the higher is the number of points of delivery of solvent, whereby the amount of deliver solvent can decrease corresponding to the actual requirements from stage to stage.

In practice, the number of points of delivery lies preferably between two and five. It depends, on the one hand, upon the composition of the hydrocarbon feed mixture, whereby a mixture with high content of non-aromates, such as e.g., pyrolysis benzene, requires more delivery points than a mixture having low aromate content, such as e.g., coking plant benzene. On the other hand, from the viewpoint of economy, it is worthwhile only with great throughput capacity of an extractive distillation column, to provide more than two delivery places, in order to limit the necessary expenditure in measuring and technical regulating apparatus within fungible bounds. In general, the greater is the capacity of an extractive distillation column, an as close as possible adaptation of the solvent delivery to the temperature behavior in the column is all the more significant. Indeed, to the extent that a better adaptation is supposed to be provided, the greater in general must be the number of regulated delivery places for the solvent.

Figure 2:
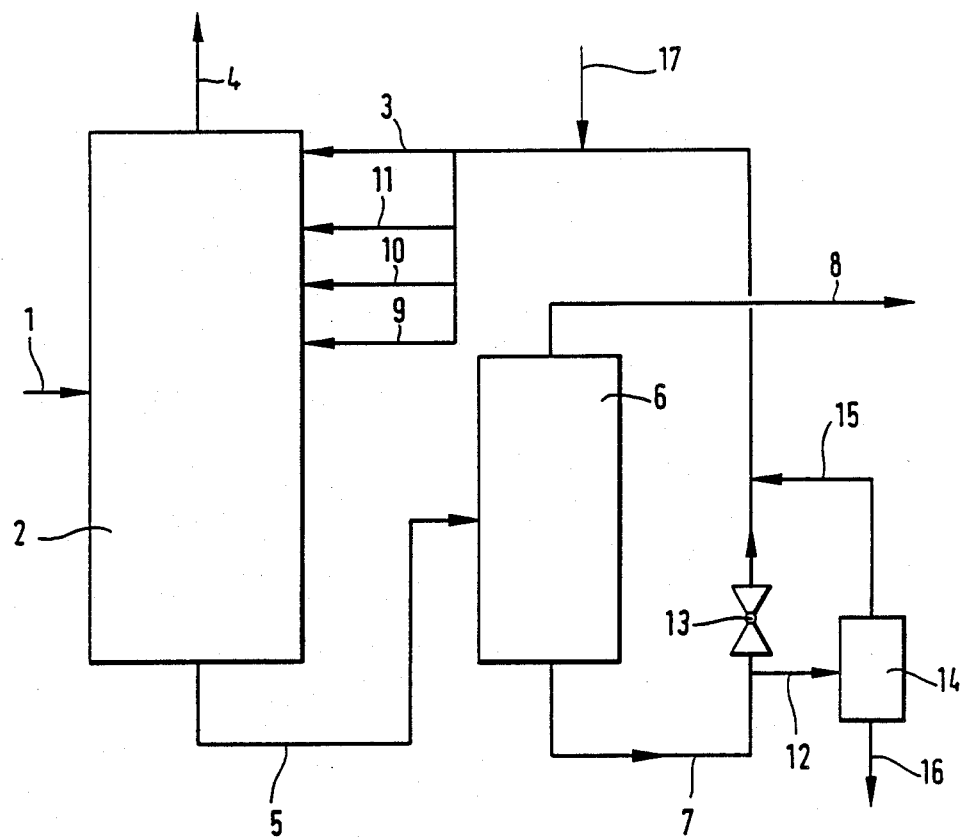
FIG. 2 is a schematic, flowchart representation of the process according to the present invention.

The technical scheme to be used for performance of the process according to the present invention is somewhat analogous to customary process schemes for extractive distillations in general. That is, the flowchart set forth in FIG. 2 is in simplified form. Therewith, the hydrocarbon mixture to be separated, which serves as feed mixture, is introduced through conduit (1) into the middle part of the extractive distillation column (2) provided with plates or similar components. In connection therewith, the feed mixture is either heated to temperatures closely below the boiling point prior to the inlet to the extractive distillation column (2), or it is introduced into the extractive distillation column (2) already in partially evaporated state. Part of the selective solvent which is delivered to the uppermost plates of this column is introduced through conduit (3). By means of conduits (9) through (11), those parts of solvent which according to the present invention are supposed to be introduced into the column above the hydrocarbon mixture inlet, are led into extractive distillation column (2). The number of three delivery points represented in FIG. 2 serves only as an example. The delivered solvent flows over the components of the extractive distillation column (2) downwardly, whereby the vaporous aromates are absorbed. The non-aromatic hydrocarbons escape through conduit (4) at the top of the column and can be condensed in a condensation arrangement not represented in the flowchart. The liquid sump product of the extractive distillation column (extract) is composed of the selective solvent and the aromates dissolved therein, and is discharged from the extractive distillation column (2) by means of conduit (5), and led into column (6) in which the aromates are separated by distillation from the selective solvent. The selective solvent is removed from the column sump by means of conduit (7) and led across conduit (3), respectively, conduits (9) through (11) back into the extractive distillation column (2), whereas the aromate vapors escape across conduit (8) at the top from column (6) and are condensed in a likewise not represented condensation arrangement and can thereafter, if necessary, be further separated.

Since over the course of time the selective solvent can become enriched with regard to impurities, branch conduit (12) is provided in the area of conduit (7), so that with appropriate regulation of valve (13) a partial amount of the selective solvent can be led to regeneration arrangement (14). The regenerated solvent is introduced through conduit (15) back into circulation (conduit 3), whereas the separated impurities are discharged through conduit (16) from regeneration arrangement (14). Conduit (17) serves for supply of fresh solvent.

The flow scheme represented in FIG. 2 does not indicate the additional arrangements which may come into use during performance of the process according to the present invention. Involved herewith are, in the first place, a heat exchanger for heating or cooling down of the individual process streams, the evaporator or circulation cooker at the sump of the individual columns, as well as the necessary measuring and regulating arrangements. However, these additional arrangements serve no role in illustration and understanding of the manner of operation according to the present invention.

Adjustment of the temperatures at which the individual partial streams of solvent are introduced into the extractive distillation column is effected expediently by mixing cold and reheated solvent together before entry into the column, to the appropriate ratio.

The advantages attainable upon practice of the process according to the present invention are summarized as follows:

Increase in the throughput capacity of an extractive distillation column in an order of about 20 percent.

Quieter, less agitated operation of the extractive distillation column. A two-phase formation at the upper plates, and therewith a jolting of the column, no longer occurs.

The residual content of aromates in the non-aromates of the raffinate is effectively lowered. In the case of benzene recovery from pressure-refined coking plant benzene, for example, the aromate content of the raffinate drops from 15 to 3 percent by weight.

The contamination of the pure aromates by particularly difficult to remove non-aromates, such as methylcyclohexane or certain other naphthenes,- recedes significantly On account of the good separation results in the extractive distillation, the running of the solvent recover column can be improved to such an extent that the loss of solvent drops to a practically insignificant amount.

DESCRIPTION OF THE PREFERRED EMBODIMENTS

COMPARISON TEST

An extractive distillation column having 60 plates is employed for this comparison test, whereby the delivery of entry product always occurs at the 30th plate. In part A of the comparison test, the total amount of solvent is delivered, in known manner, to the uppermost plate of the extractive distillation column. In part B of the comparison test, according to the present invention, in contrast 37.5% by weight of the total amount of solvent, distributed in two partial streams, is introduced into the extractive distillation column at plates above the hydrocarbon mixture inlet. Obviously, a mixture having the same composition is employed in the extractive distillation column in both parts of the comparison test, as well as the same extractive distillation column. N-formylmorpholine (NFM) is employed in each case as selective solvent. The obtained test results are summarized in the following table, with the numerical designations referring to the flow scheme of FIG. 2

| PART A: | Input through conduit 1: | 750 kg/h benzene |
| --- | --- | --- |
| | | 150 kg/h paraffin |
| | | 100 kg/h naphthene |
| | | 1000 kg/h |
| | Solvent through conduit 3: | 4000 kg/h NFM |
| | | 40 kg/h benzene |
| | | 4040 kg/h |
| | Sump product through conduit 5: | 4000.00 kg/h NFM |
| | | 765.00 kg/h benzene |
| | | 0.25 kg/h paraffin |
| | | 0.50 kg/h naphthene |
| | | 4765.75 kg/h |
| | Top product through conduit 4: | 149.75 kg/h paraffin |
| | | 99.50 kg/h naphthene |
| | | 25.00 kg/h benzene |
| | | 274.25 kg/h |
| PART B: | Hydrocarbon mixture through conduit 1: | 900 kg/h benzene |
| | | 180 kg/h paraffin |
| | | 120 kg/h naphthene |
| | | 1200 kg/h |
| | Solvent through conduit 3: | 3000 kg/h NFM |
| | | 30 kg/h benzene |
| | Solvent through conduit 9: (3rd plate above hydrocarbon mixture inlet) | 1000 kg/h NFM |
| | | 10 kg/h benzene |
| | Solvent through conduit 10: (5th plate above hydrocarbon mixture inlet) | 800 kg/h NFM |
| | | 8 kg/h benzene |
| | Sump product through conduit 5: | 4800.00 kg/h NFM |
| | | 936.00 kg/h benzene |
| | | 0.30 kg/h paraffin |
| | | 0.40 kg/h naphthene |
| | | 5736.70 kg/h |
| | Top product through conduit 4: | 179.7 kg/h paraffin |
| | | 119.6 kg/h naphthene |
| | | 12.0 kg/h benzene |
| | | 311.3 kg/h |

A numerical comparison confirms the above stated advantages of the process according to the present invention. Thus, with use of the process, despite employment of the same extractive distillation column, the hydrocarbon mixture feed is increased about 20% per hour. Simultaneously, the benzene content in the top product (raffinate) drops from 9.12% to 3.85%, while the content of non-aromates in the benzene recovered in the sump product (extract) drops from 0.098% to 0.075%.

EXAMPLE

ADJUSTMENT OF SOLVENT TEMPERATURE

As mentioned, supra, the temperature of solvent delivered to the column can be adjusted by mixing heated solvent with cold solvent, prior to or at the solvent delivery location. The following are representative examples:

| 1. | Necessary amount of solvent at delivery plates: | 10 t/h |
| --- | --- | --- |
| | Temperature of the cold solvent | 100° C. |
| | Temperature of the hot solvent | 150° C. |
| | Temperature to be adjusted | 125° C. |
| | Amount of cold solvent | 5 t/h |
| | Amount of hot solvent | 5 t/h |
| 2. | Necessary amount of solvent at delivery plates: | 10 t/h |
| | Temperature of the cold solvent | 100° C. |
| | Temperature of the hot solvent | 150° C. |
| | Temperature to be adjusted | 140° C. |
| | Amount of cold solvent | 2 t/h |
| | Amount of hot solvent | 8 t/h |

It will be understood that each of the elements described above, or two or more together, may also find a useful application in other types of hydrocarbon techniques differing from the types described above.

While the invention has been illustrated and described as embodied in a process for the separation of aromates from hydrocarbon mixtures of optional aromate content, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt if for various applications without omitting features that, from the standpoint of prior art, fairly constitute essential characteristics of the generic or specific aspects of this invention.

We claim:

1. Process for the separation of aromatic hydrocarbons from a hydrocarbon mixture by means of extractive distillation employing N-substituted morpholine, substitutions of which have no more than 7 carbon atoms, as selective solvent, only a part of the requisite total amount of solvent being delivered in substantially pure form to an uppermost plate of an extractive distillation column, comprising introducing a hydrocarbon mixture as a feed to an intermediate inlet of the column distributing the remainder of said requisite total amount of solvent into at least two partial streams, introducing said at least two partial streams each in substantially pure solvent form into said extractive distillation column onto plates above said inlet for said hydrocarbon mixture and adjusting the introduction temperature of said respective partial streams so as not to exceed the temperature of said plates above said hydrocarbon mixture inlet and also not to fall more than 10° C. below said temperature.

2. The process according to claim 1, wherein said remainder of said requisite total amount of solvent which is not deliverd to the uppermost plate of the extractive distillation column amounts to between 10 and 40% by weight of said requisite total amount of solvent.

3. The process according to claim 1, wherein said remainder of said requisite total amount of solvent which is not delivered to the uppermost plate of the extractive distillation column is distributed into between two and five partial streams.

4. The process according to claim 1, wherein introduction of said partial streams of solvent into said extractive distillation column is effected from the third to the tenth plate above said hydrocarbon mixture inlet.

5. The process according to claim 1, further comprising the amount of solvent introduced into said extractive distillation column by means of said partial streams decreases from stage to stage in the direction of the uppermost plate.

* * * * *